United States Patent [19]

Kaplan et al.

[11] Patent Number: 4,680,389
[45] Date of Patent: Jul. 14, 1987

[54] TEMPERATURE STABLE CRYSTALLINE DI(1-METHYL-2-PYRRALIDINONE) AND DI(N-FORMYLPYRROLIDINE) ADDUCTS OF CEPHALOSPORIN DERIVATIVES

[75] Inventors: Murray A. Kaplan, Syracuse; Joseph B. Bogardus; Robert A. Lipper, both of Manlius, all of N.Y.

[73] Assignee: Bristol-Myers Company, New York, N.Y.

[21] Appl. No.: 817,646

[22] Filed: Jan. 10, 1986

[51] Int. Cl.$^4$ .......................................... C07D 501/46
[52] U.S. Cl. ................................................. 540/222
[58] Field of Search ........................... 544/22; 514/202

[56] References Cited

U.S. PATENT DOCUMENTS 4,318,852  3/1982  Heitman et al. ................. 260/239.1
4,406,899  9/1983  Aburaki et al. ..................... 424/246

FOREIGN PATENT DOCUMENTS 0131147  4/1986  European Pat. Off. .

*Primary Examiner*—Donald G. Daus
*Assistant Examiner*—Barbara Cassatt
*Attorney, Agent, or Firm*—Robert E. Carnahan

[57] ABSTRACT

Crystalline adducts of 7-[(Z)-2-methoxyimino-2-(2-aminothiazol-4-yl)acetamido-3-[(1-methyl-1-pyrrolidinium)methyl]-3-cephem-4-carboxylate selected from the group consisting of the di(1-methyl-2-pyrrolidinone) adduct and the di(N-formyl pyrrolidine) adduct and salt complexes thereof have been found to be stable at even high temperatures. The crystalline adducts are prepared by forming an admixture of adducting agents, zwitterions and seed adduct crystals and inducing crystallization followed by isolating the crystals. A process for preparing adduct salt complexes is also disclosed. Crystalline zwitterion can be formed by slurrying the adducts in a solvent which removes the adducting agents.

4 Claims, 2 Drawing Figures

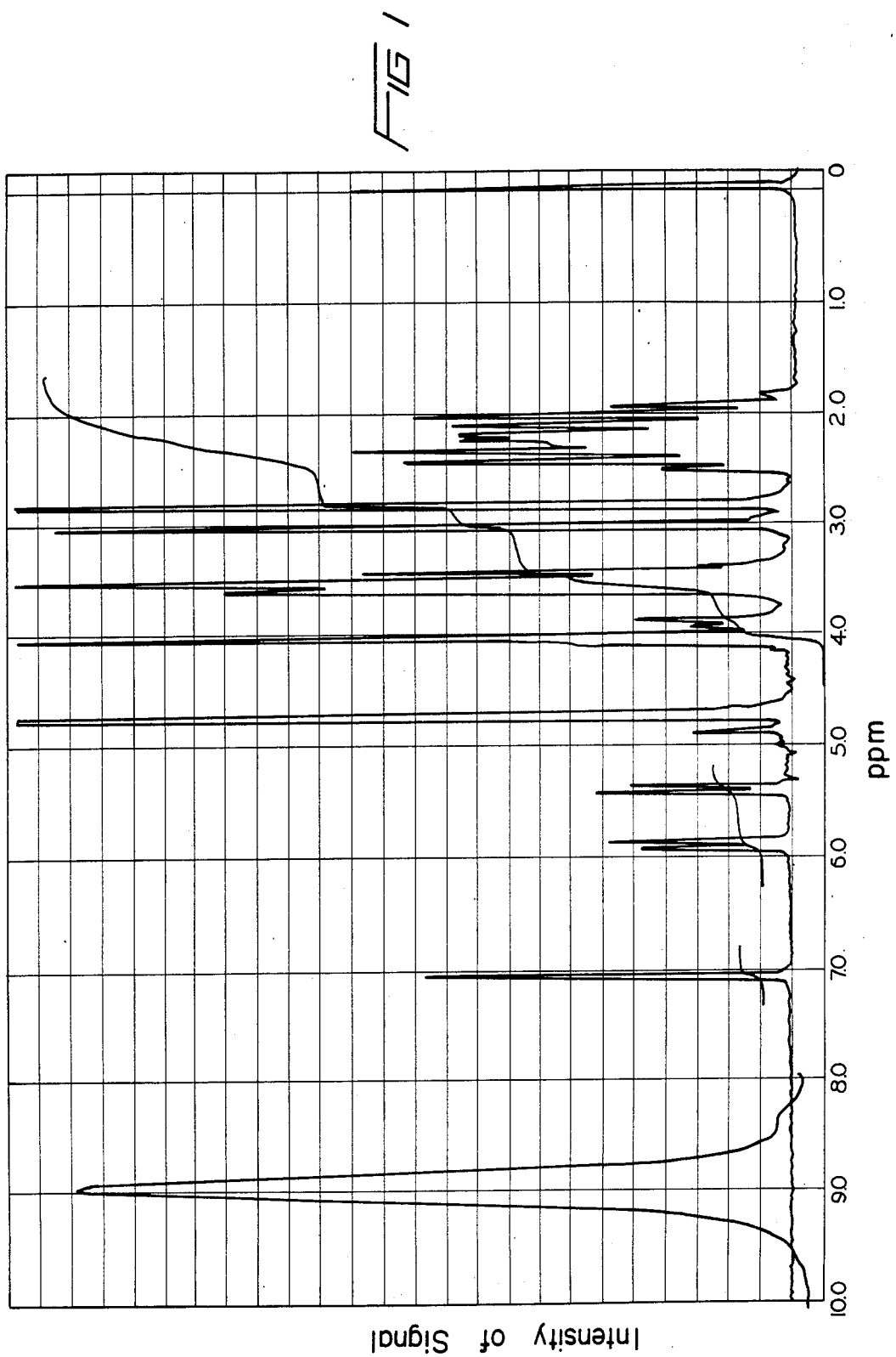

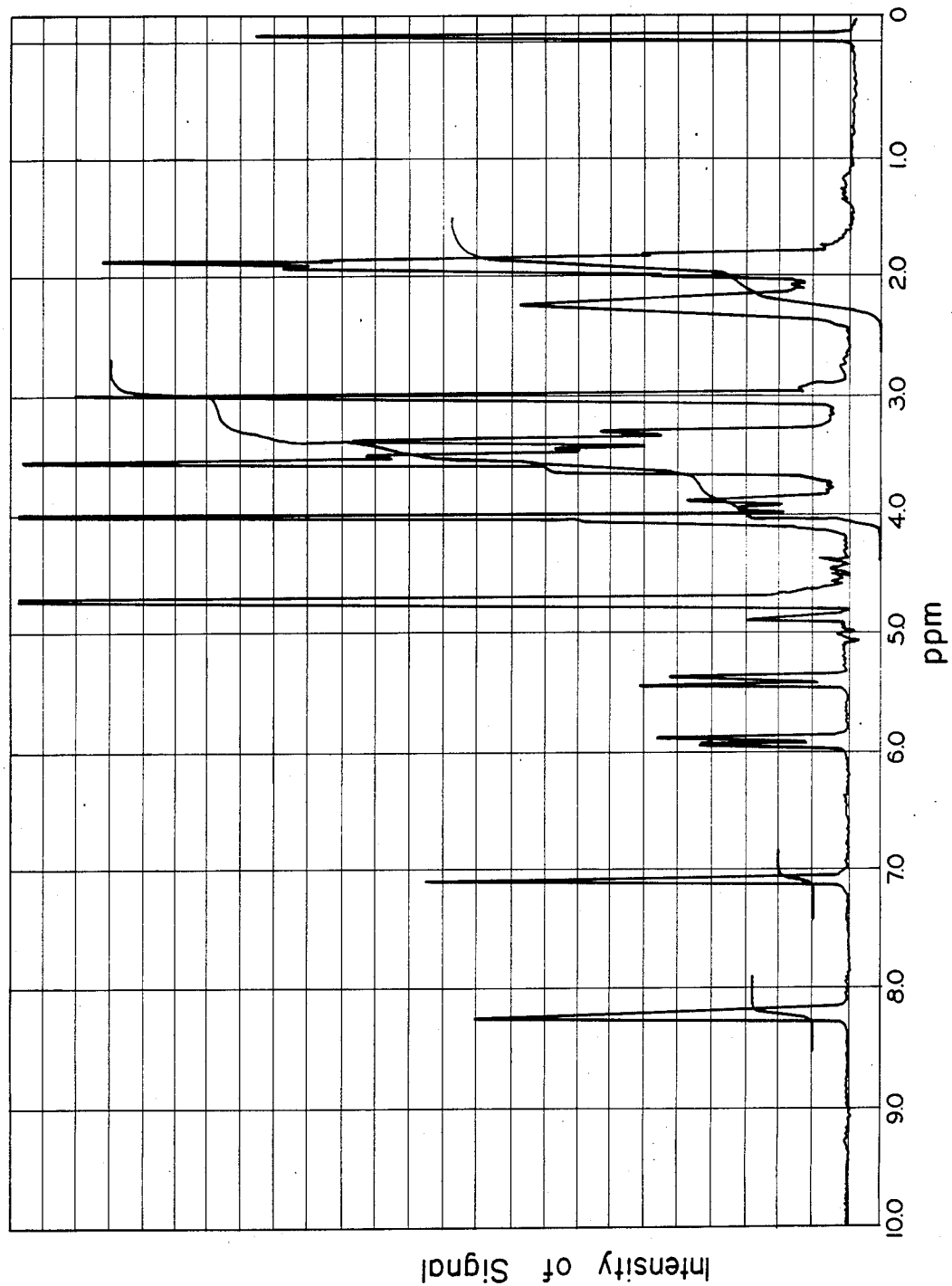

TEMPERATURE STABLE CRYSTALLINE DI(1-METHYL-2-PYRRALIDINONE) AND DI(N-FORMYLPYRROLIDINE) ADDUCTS OF CEPHALOSPORIN DERIVATIVES

TECHNICAL FIELD

This invention is directed to temperature stable crystalline di(1-methyl-2-pyrrolidinone) and di(N-formylpyrrolidine) adducts of cephalosporin derivatives and corresponding salt complexes, and to the preparation of such adducts and corresponding salt complexes.

BACKGROUND OF THE INVENTION

Aburaki et al. U.S. Pat. No. 4,406,899 discloses 7-[(Z)-2-methoxyimino-2-(2-aminothiazol-4-yl)acetamido]-3-[(1-methyl-1-pyrrolidinium)methyl]-3-cephem-4-carboxylate in the zwitterion form and mentions corresponding acid addition salts (which are present in the zwitterion form in injectable compositions) and shows that the zwitterion form has broader spectrum activity than ceftazidime and cefotaxime.

However, the aforementioned Aburaki et al. cephalosporins are stable only for a few hours as injectable compositions and the zwitterion form even as a dry powder is unstable at room temperature and loses 30% or more of its activity on storage at elevated temperatures (e.g. 45° C. and above) for even one week.

Crystalline acidic salts, such as $H_2SO_4$ salts, of the zwitterion are high temperature stable but are too acidic for intramuscular and intravenous use and somewhat excessive quantities of varied bases and buffering agents are required to obtain physiologically acceptable pH ranges (3.5–7.0) with the acidic salts.

SUMMARY OF THE INVENTION

It has been discovered herein that certain crystalline adducts of 7-[(Z)-2-methoxyimino-2-(2-aminothiazol-4-yl)acetamido]-3-[(1-methyl-1-pyrrolidinium)methyl]-3-cephem-4-carboxylate (also known as (7-[α-(2-aminothiazol-4-yl)-α-(2)-methoximino-acetamido]-3-[(1-methyl-1-pyrrolidinio)-methyl)-3-cephem-4-carboxylate) in dry powder form have excellent room temperature stability and have superior elevated temperature stability compared to the zwitterion form. The term "dry powder form" as used herein means a moisture content of less than 5% by weight.

The crystalline adducts of 7-[(Z)-2-methoxyimino-2-(2-aminothiazol-4-yl)acetamido]-3-[(1-methyl-1-pyrrolidinium)methyl]-3-cephem-4-carboxylate are selected from the group consisting of the di(1-methyl-2-pyrrolidinone) adducts and the di(N-formylpyrrolidine) adducts, or hydrates thereof and salt complexes. The term "complex" is used herein to mean the composition formed by addition of a selected salt, preferably sodium chloride in the adduct forming process as described hereinafter whereby the salt is included in the ultimate composition.

The adducts of the instant invention can be converted to provide a crystalline zwitterion which is more temperature stable than the amorphous form and which has the structure (hereinafter referred to as the zwitterion):

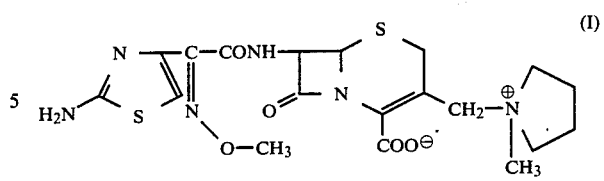

The crystalline adducts and salt complexes herein when formed into aqueous injectable compositions provide the zwitterion (I) in solution.

The broad spectrum utility against various organisms of the zwitterion form, and thus the aqueous compositions made up from the adducts and the adduct salt complexes herein, is shown by the data in Aburaki et al. U.S. Pat. No. 4,406,899 which is hereby incorporated by reference.

Aqueous compositions are made up from the adducts herein simply by the additions of sterile water. These adducts may also be administered as salt complexes such as with NaCl.

DESCRIPTION OF THE DRAWINGS

The following are presented in the drawings:

FIG. 1—$^1H$—NMR spectrum of di(1-methyl-2-pyrrolidinone) adduct at 90 MHz in $D_2O$ solution, TSP=O.

FIG. 2—$^1H$—NMR spectrum of di(N-formyl-pyrrolidine) adduct at 90 MHz in $D_2O$ solution, TSP=O.

DETAILED DESCRIPTION OF THE INVENTION

The heterocyclic adducts hereinafter referred to simply as the adducts, of the instant invention are represented by the following structural formulas:

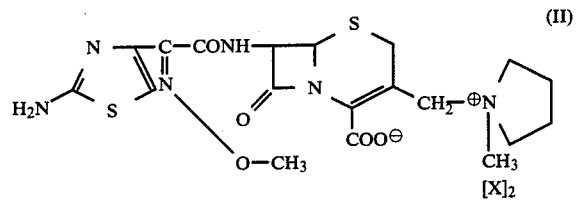

wherein X is either

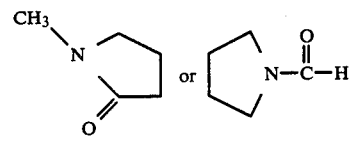

The cephalosporin derivatives having substituent (1) will henceforth be identified as the di(1-methyl-2-pyrrolidinone) adduct and those derivatives having substituent (2) will henceforth be identified as the di(N-formyl pyrrolidine) adduct.

Hereinafter both 1-methyl-2-pyrrolidinone (sometimes referred to as NMP-2) and N-formyl pyrrolidine (sometimes referred to as NFP) may be referred to as adducting agents.

The crystalline adducts of the instant invention have excellent stability at low, room and elevated temperatures and have a predicted shelf life, i.e. they display less than 10% potency loss for at least one to three years at 25° C., i.e. room temperature. These crystalline adducts display acceptable stability when they are placed in solution. Typically, a 250 mg/ml aqueous solution of the di(1-methyl-2-pyrrolidinone) adduct of 7-[(Z)-2-methoxyimino-2-(2-aminothiazol-4-yl)acetamido-]3-[(1-methyl-1-pyrrolidinium)methyl]-3-cephem-4-carboxylate at an ambient pH of 4 to 5 is stable with less than 10% potency loss for at least six hours at 25° C.

We now turn to the preparation of the adducts herein.

The adducts of the present invention are optionally prepared by a process comprising the steps of:

(a) forming an admixture of (i) at least two molar equivalents of an adducting agent and (ii) zwitterion in an amount so as to be present in the admixture at a concentration of greater than 10 mg/ml, (b) causing crystallization to occur, and (c) isolating the crystalline adduct.

Step (a) is readily carried out by adding solid zwitterion to the selected adducting agent, i.e. 1-methyl-2-pyrrolidinone or N-formyl-pyrrolidine.

Step (b) is carried out by inducing crystallization, preferably by seeding with the appropriate crystalline adduct and then slurrying preferably for 4 to 6 hours at approximately 20°-25° C. It is preferred that the crystallization step be carried out in an organic media which is free of water.

Step (c) is carried out by separating the crystals from the crystallization medium, preferably by vacuum filtration, then washing e.g. with portions of the selected adduct agent, i.e. 1-methyl-2-pyrrolidinone or N-formyl-pyrrolidine, and then drying, e.g. by high vacuum drying at 45°-55° C. for 1-4 hours. Alternatively the crystals on the filter can be washed, e.g. with three 5 ml portions of ethyl ether and then vacuum dried at 40°-50° C. for 1-2 hours.

Preferably the zwitterion is used in step (a) in an amount so as to be present in the admixture at a concentration ranging from about 10 mg/ml to about 100 mg/ml, and step (b) is carried out in an organic media. Normally 2 molar equivalents of either 1-methyl-2-pyrrolidinone or N-formyl-pyrrolidine are utilized in step (a) and the zwitterion in step (b) is utilized in an amount so as to be present in the admixture at a concentration greater than 10 mg/ml.

In an alternative preferred process to the above process steps (a) and (b), are replaced by the following steps. Seed crystals of the adduct are first added to the adducting agent followed by rapid stirring during the addition of zwitterion. The mixture is then slurried for 4 to 16 hours at 20°-25° C. Step (c) is then followed according to the above procedures.

The 1-methyl-2-pyrrolidinone adducts of the instant invention may also be complexed with NaCl. A 1-methyl-2-pyrrolidinone adduct NaCl complex is prepared as follows. An aqueous solution of at least 25-250 mg/ml of zwitterion is mixed with at least 1.0 molar equivalent of NaCl and the mixture is lyophilized or precipitated with isopropanol. A 50-100 mg/ml of the zwitterion-1-methyl-2-pyrrolidinone-NaCl adduct in 1-methyl-2-pyrrolidinone is slurried for 4-16 hours at 22°-26° C. The resultant suspension is filtered, washed with ⅓ volume of 1-methyl-2-pyrrolidinone, ½ volume of ether followed by vacuum drying at 50° C. 2 hours to produce stable, crystalline, 1-methyl-2-pyrrolidinone adduct NaCl complex, normally having 1.3 moles of 1-methyl-2-pyrrolidinone and 1.0 mole of NaCl per 1.0 molar equivalent of zwitterion in the complex.

It is noted that the adducts of the instant invention as well as the 1-methyl-2-pyrrolidinone adduct NaCl-complex can be readily converted to a crystalline zwitterion of formula I by slurrying them in a suitable solvent, i.e. a solvent which dissolves the adducting agent, such as methylene chloride, acetone or isopropanol, at a temperature ranging from 0° C. to 30° C. for 2 to 6 hours. The crystalline zwitterion is readily recovered, e.g. by vacuum filtration. This method of crystallization appears to be unique as an amorphorus zwitterion for formula I does not convert to the crystalline form when similarly slurried in solvents in the presence of other seed crystals and has defied crystallization, except by the above described procedure.

The adducts of the present invention, as well as the zwitterions prepared from these adducts, are markedly more stable than the zwitterions prepared in accordance with U.S. Pat. No. 4,406,899. Furthermore the adducts of the present invention can be dissolved in water for use in intravenous, intramuscular or subcutaneous dosage form. No significant irritation to animal models has been noted as has been previously noticed through the use of other buffered salts of the zwitterion. The adducts and complexes of the instant invention are readily shipped and stored in solid form thereby taking advantage of the stability of the solid form of the adducts. The adducts are readily converted into an injectable composition simply by the addition of sterile water, e.g. by a nurse or doctor just prior to use. The adducts herein can be stored without refrigeration or insulated packaging and still retain high potency.

The adducts and NaCl complex thereof or the crystalline zwitterion herein are formed into injectable compositions by diluting with sterile water to form an injectable concentration of up to 400 mg/ml of adduct or zwitterion. For intramuscular or intravenous administration to an adult human, a total dosage of from about 750 to about 3000 mg per day in divided doses is normally sufficient.

In several of the preparations herein the unstable amorphous zwitterion is used as the starting material. The preparation of this is described in examples 1–3 of Aburaki et al. U.S. Pat. No. 4,406,899. The zwitterion is referred to in Aburaki et al. as 7-[(Z)-2-methoxyimino-2-(2-aminothiazol-4-yl)acetamido]-3-[(1-methyl-1-pyrrolidinium)methyl]-3-cephem-4-carboxylate.

The invention is illustrated in the following working examples.

EXAMPLE 1

Preparation of the Di(1-Methyl-2-Pyrrolidinone) Adduct 1.0 g of the sulfuric acid addition salt of the zwitterion is vigorously slurried in 10 ml of 1-methyl-2-pyrrolidinone (NMP-2) at 25° C.–45° C. The crystalline mass is mixed with 0.49 ml (2.02 molar equivalents) of triethylamine (TEA) over a period of 0.5 to 1.5 hours. The mixture is seeded with 1-methyl-2-pyrrolidinone adduct and vigorously stirred for 6 to 24 hours. The crystals are then separated by vacuum filtration, washed with two 3 ml portions of 1-methyl-2-pyrrolidinone, two 5 ml portions of ether and vacuum dried at 45° to 55° C. for 2 hours.

A typical yield is 0.8–0.85 g of di(1-methyl-2-pyrrolidinone) adduct which displays the following physical parameters (HPLC represents High Performance Liquid Chromatography):

| | |
|---|---|
| Percent H₂O, (Karl Fischer) = | 0.6% |
| HPLC Potency = | 681 mcg/mg (theory = 708 mcg/mg) or 96.8% of theory on a dry basis. |
| Free NMP* (NMR) = | 0.2% |
| Total NMP (NMR) = | 1 mole equivalent |
| Total (NMP-2) (NMR) = | 2 mole equivalents |
| SO₄⁼ = | 0.16% |
| Amount TEA (NMR) | Trace |
| HPLC Stability | % Loss |
| 1 Day; 70° C. | 0–2.3 |
| 3 Days; 70° C. | 5–6.5 |

*N—methyl pyrrolidine

EXAMPLE 2
Preparation of Di(1-Methyl-2-Pyrrolidinone) Adduct

Seed crystals of di(1-methyl-2-pyrrolidinone) adduct are added to 10 ml of 1-methyl-2-pyrrolidinone. During rapid stirring 1 g of zwitterion is sprinkled into the mixture over a 10 minute interval. The mixture is slurried for 4 to 16 hours at 20° to 25° C. The crystals are separated by vacuum filtration and the filter cake is tamped to remove any cracks if present. The crystals are washed with two 3.5 ml portions of 1-methyl-2-pyrrolidinone, two 5 ml portions of ether and vacuum dried at 45°–55° C. for 2 hours. The recovered yield is 1 gram of crystalline di(1-methyl-2-pyrrolidinone) adduct.

Analysis of compounds which were prepared according to this procedure is as follows: Calculated for $C_{29}H_{42}N_6O_5S_2$ (M.W.=678.84): %C, 51.31; %H, 6.23; %N, 16.51; %S, 9.45; %H₂O, none. Found: %C, 51.04; %H, 6.38; %N, 16.30; %S, 9.26, %H₂O, 0.32, % residue (sulfated ash), <0.1.

The di(1-methyl-2-pyrrolidinone) adduct prepared by the above procedures has the following structural formula:

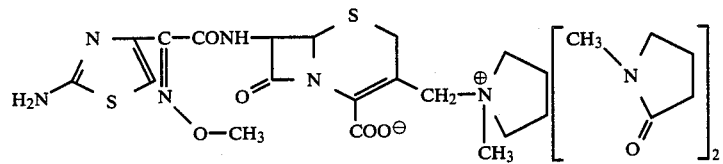

The NMR spectrum (¹H, 90 MHz, in D₂O solution) of the di(1-methyl-2-pyrrilidinone) adduct is shown in FIG. 1 and displays the following characteristics:

| CHEMICAL SHIFT PPM δ, TSP = O | DESCRIPTION | INTEGRAL | ASSIGNMENT |
|---|---|---|---|
| 1.8–2.6 | Multiplet | 12 | $C_{14}\underline{H}_2,C_{14'}\underline{H}_2$, $C\underline{H}_2$(1-Methyl-2 Pyrrolidinone) |
| 2.84 | Singlet | 6 | $C\underline{H}_3N$ (1-Methyl-2 Pyrrolidinone) |
| 3.02 | Singlet | 3 | $C_{12}\underline{H}_3$ |
| 3.2–3.7 | Multiplet | 9 | $C_2\underline{H},C_{13}\underline{H}_2,C_{13}\underline{H}_2$, $C\underline{H}_2N$ (1-Methyl-2 Pyrrolidinone) |
| 3.8–4.1 | Overlapping Doublets | 2 | $C_2\underline{H},C_{11}\underline{H}$ |
| 4.04 | Singlet | 3 | $C_{20}\underline{H}_3$ |
| 4.8 | Doublet | 1 | $C_{11}\underline{H}$ |
| 5.38 | Doublet | 1 | $C_6\underline{H}$ |
| 5.88 | Doublet | 1 | $C_7\underline{H}$ |
| 7.06 | Doublet | 1 | $C_{18}\underline{H}$ |

EXAMPLE 3
Conversion of Crystalline Di(1-methyl-2-Pyrrolidinone) Adduct To Crystalline Zwitterion 1 gram of di(1-methyl-2-pyrrolidinone) adduct is vigorously slurried in a closed system in 10 to 50 ml of either acetone or methylene chloride or isopropanol at 20°–25° C. for 2 to 4 hours. The resultant microcrystalline zwitterion is recovered by vacuum filtration. The recovered zwitterion crystals are washed with two 10 ml portions of either acetone or methylene chloride and dried under high vacuum for two hours at 20°–25° C. The expected yield is 0.6 to 0.7 g of crystalline zwitterion which should be stored at −20° C. or lower.

EXAMPLE 4
Preparation of Crystalline Di(N-Formyl Pyrrolidine) Adduct

Seed crystals of di(N-formyl pyrrolidine) adduct are added to 10 ml of N-formyl pyrrolidine. During rapid stirring, 1 g of zwitterion is sprinkled into the mixture over a 10 minute interval. The mixture is slurried for 4 to 16 hours at 20° to 25° C. The crystals are separated by vacuum filtration and the filter cake is tamped to remove any cracks if present. The crystals are washed with two 3.5 ml portions of N-formyl pyrrolidine, two 5 ml portions of ether and vacuum dried at 45°–55° C. for two hours. The recovered yield is 1 gram of crystalline di(N-formyl pyrrolidine) adduct.

The NMR spectrum (¹H, 90 MHz, in D₂O solution) of the di(N-formyl pyrrolidine) adduct in shown in FIG. 2 and displays the following characteristics:

| CHEMICAL SHIFT PPM δ, TSP = O | DESCRIPTION | INTEGRAL | ASSIGNMENT |
|---|---|---|---|
| 1.7–2.08 | Multiplet | 8 | $C\underline{H}_2C\underline{H}_2$ (N—Formyl Pyrrolidine) |
| 2.08–2.4 | Multiplet | 4 | $C_{14}\underline{H}_2C_{14'}\underline{H}_2$ |
| 3.02 | Singlet | 3 | $C_{12}\underline{H}_3$ |
| 3.2–3.75 | Multiplet | 13 | $C_{13}\underline{H}_2,C_{13'}\underline{H}_2,C_2\underline{H}$, $C\underline{H}_2NC\underline{H}_2$ (N—Formyl Pyrrolidine) |
| 3.8–4.1 | Overlapping Doublets | 2 | $C_2\underline{H},C_{11}\underline{H}$ |
| 4.04 | Singlet | 3 | $C_{20}\underline{H}_3$ |
| 4.8 | Doublet | 1 | $C_{11}\underline{H}$ |
| 5.4 | Doublet | 1 | $C_6\underline{H}$ |
| 5.9 | Doublet | 1 | $C_7\underline{H}$ |

| CHEMICAL SHIFT PPM δ, TSP = O | DESCRIPTION | INTE-GRAL | ASSIGNMENT |
|---|---|---|---|
| 7.08 | Singlet | 1 | $C_{18}H$ |
| 8.2 | Singlet | 2 | $NC\underline{H}$ (N—Formyl Pyrrolidine) |

This adduct is readily converted to the crystalline zwitterion by substituting an equivalent amount for the di(1-methyl-2-pyrrolidinone) adduct in Example 3.

EXAMPLE 5

Preparation of 1-Methyl-2-Pyrrolidinone Adduct-NaCl Complex 1 g of lyophilized zwitterion-NaCl complex (1/1 molar ratio) is mixed with 20 ml of 1-methyl-pyrrolidinone. Crystallization is then induced by seeding stirring for 6-16 hours at 24° C. The crystals are recovered from the resultant slurry by vacuum filtration, washed with two 5 ml portions of 1-methyl-2-pyrrolidinone, three 5 ml portions of ethyl ether and vacuum dried at 45°-55° C. for 2 hours. The typical yield is 1 g of 1-methyl-2-pyrrolidinone adduct-NaCl complex containing 1.3 moles of 1-methyl-pyrrolidinone and 1.0 mole of NaCl per 1.0 mole of zwitterion in the complex.

EXAMPLE 6

Stabilities at Elevated Temperatures

Elevated temperature stabilities were determined by storing the preparations in dry containers (1 dram screw cap vials) at temperatures and for time periods as denoted below. Potency losses or gains were determined by HPLC. A less than 10% potency loss over a 2 to 4 week period at 45°-56° C. indicates a less than 10% potency loss over a 1-3 year period at room temperature. Each compound form tested was prepared in accordance with the example which is designated.

| FORM | 100° C. 1 Day | 70° C. DAYS | | | | 56° C. WEEKS | | | | | 45° C. WEEKS | | | | | 37° C. MONTHS | | |
|---|---|---|---|---|---|---|---|---|---|---|---|---|---|---|---|---|---|---|
| | | 1 | 2 | 3 | 5 | 1 | 2 | 4 | 6 | 8 | 1 | 2 | 4 | 6 | 8 | 1 | 2 | 3 |
| Zwitterion (Amorphous) | 100 | 34.5 | 46.2 | 55.2 | | 49.6 | | | | | 34.1 | | 71 | | | | | |
| Zwitterion (Crystalline) | | | 13.5 | 20.5 | | 25.6 | 30.0 | | | | 14.2 | 23.0 | | | | 20.0 | | |
| Example 3 Di (NMP-2) Adduct | 13-16 | 0 | 2.1 | 2.1 | 2.1 | 2.1 | 3.4 | 4.2 | 7.0 | 0.9 | | | 1.6 | 3.0 | 0-3 | | | 1.2 |
| Example 2 Di(NFP) Adduct | | 1.5 | | 0-4.4 | | 7.1 | 9.3 | 18.1 | | | 0-3 | | 3.5-5.9 | | | 0 | | |
| Example 4 NMP-2 Adduct NaCl Complex Example 5 | 4-16 | 1.4 | 1.8 | 1.5 | | 3.2 | 4.3 | 7.6 | | | 0 | 1.8 | 4.3 | | | 4.0 | | |

EXAMPLE 7

Toxicity Data

Toxicity data (LD$_{50}$) was determined for the following compounds which are utilized in the instant invention or prepared according to the instant invention.

| SUBSTANCE | Rat LD$_{50}$ (mg/kg) |
|---|---|
| 1-Methyl-2-pyrrolidinone | >2000, <2500 |
| N—Formyl pyrrolidine | >500, <1000 |
| Zwitterion | 665 |
| Di(1-methyl-2-pyrrolidinone) adduct | 663 |
| Di(N—formyl pyrrolidine) adduct | 495 |

What is claimed is:

1. High temperature stable crystalline adducts of 7-[(Z)-2-methoxyimino-2-(2-aminothiazol-4-yl)acetamido]-3-[(1-methyl-1-pyrrolidinium)methyl]-3-cephem-4-carboxylate selected from the group consisting of the di(1-methyl-2-pyrrolidinone) adduct, di(N-formyl-pyrrolidine) adduct, and 1-methyl-2-pyrrolidinone adduct-NaCl complex.

2. The crystalline adducts of claim 1 represented by the structural formula:

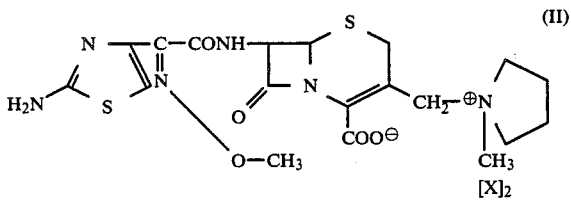

wherein X is either

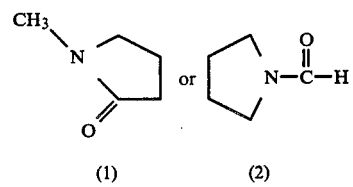

3. The crystalline adducts of claim 1 wherein the adduct is a salt complex consisting of one molar equivalent of 7-[(Z)-2-methoxyimino-2-(2-aminothiazol-4-yl)acetamido]-3-[(1-methyl-1-pyrrolidinium)methyl]-3-cephem-4-carboxylate per 1.3 moles of 1-methyl-2-pyrrolidinone and 1.0 mole of NaCl.

4. A method for preparing a 7-[(Z)-2-methoxyimino-2-(2-aminothizol-4-yl)acetamido]-3-[(1-methyl-1-pyrrolidinium)methyl]-3-cephem-4-carboxylate (1-methyl-2-pyrrolidinone) adduct-NaCl complex comprising:

(a) admixing 10-100 mg/ml of lyphilized zwitterion-NaCl complex in 1-methyl-2-pyrrolidinone, (b) inducing crystallization with seed crystals of a 1-methyl-2-pyrrolidinone adduct-NaCl, and (c) isolating the (1-methyl-2-pyrrolidinone) adduct-NaCl complex.

* * * * *